(12) United States Patent
Bissinger et al.

(10) Patent No.: US 6,852,795 B2
(45) Date of Patent: Feb. 8, 2005

(54) PREPOLYMERIC (METH)ACRYLATES WITH POLYCYCLIC OR AROMATIC SEGMENTS

(75) Inventors: Peter Bissinger, Diessen (DE); Gunther Eckhardt, Bad Dürrenberg (DE); Wolfgang Weinmann, Gilching (DE)

(73) Assignee: 3M ESPE AG, Seefeld (DE)

( * ) Notice: Subject to any disclaimer, the term of this patent is extended or adjusted under 35 U.S.C. 154(b) by 0 days.

(21) Appl. No.: 10/296,491

(22) PCT Filed: May 29, 2001

(86) PCT No.: PCT/EP01/06100

§ 371 (c)(1),
(2), (4) Date: Jan. 27, 2003

(87) PCT Pub. No.: WO01/92271

PCT Pub. Date: Dec. 6, 2001

(65) Prior Publication Data

US 2003/0166816 A1 Sep. 4, 2003

(30) Foreign Application Priority Data

May 29, 2000 (DE) .......................................... 100 26 432

(51) Int. Cl.⁷ .............................................. C08L 83/07
(52) U.S. Cl. ........................ 524/588; 526/279; 523/109
(58) Field of Search ........................ 524/588; 526/279; 523/109

(56) References Cited

U.S. PATENT DOCUMENTS

| 4,702,990 A |   | 10/1987 | Tanaka et al. |
| 4,760,122 A |   | 7/1988 | Nakos et al. |
| 4,843,136 A | * | 6/1989 | Reiners et al. |
| 5,081,164 A |   | 1/1992 | Lai |
| 5,412,055 A |   | 5/1995 | Loo |
| 6,566,413 B1 | * | 5/2003 | Weinmann et al. |
| 6,624,236 B1 | * | 9/2003 | Bissinger et al. ............ 524/588 |

FOREIGN PATENT DOCUMENTS

| DE | 37 07 908 A1 | 3/1988 |
| DE | 198 60 361 A1 | 6/2000 |
| DE | 198 60 364 A1 | 6/2000 |
| DE | 199 34 407 A1 | 1/2001 |
| EP | 0 261 520 A2 | 3/1988 |
| EP | 0 358 584 A1 | 3/1990 |
| JP | 60-57833 A | 4/1985 |
| JP | 62-165644 A | 7/1987 |
| JP | 0 422 319 A2 | 4/1991 |
| JP | 0 423 688 A2 | 4/1991 |
| JP | 0 423 689 A2 | 4/1991 |

OTHER PUBLICATIONS

International Search Report.

German Office Action.

Gao, Feng, et al. Polymer Preprints. vol. 41, No. 1, 2000, pp. 580–581.

* cited by examiner

*Primary Examiner*—Kuo-Liang Peng
(74) *Attorney, Agent, or Firm*—Birch, Stewart, Kolasch & Birch, LLP

(57) ABSTRACT

The invention relates to monomers according to the formulae:

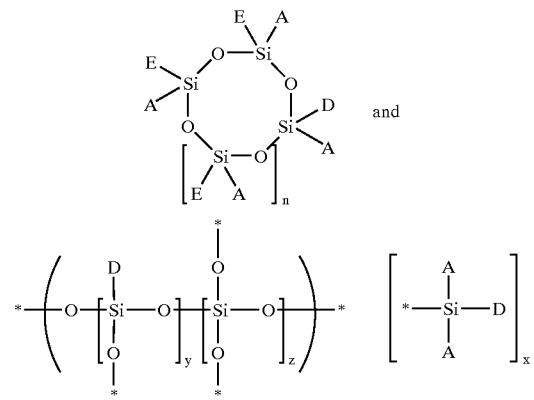

as well as curable materials containing these monomers.

13 Claims, No Drawings

PREPOLYMERIC (METH)ACRYLATES WITH POLYCYCLIC OR AROMATIC SEGMENTS

This application is the national phase under 35 U.S.C. § 371 of PCT International Application No. PCT/EP01/06100 which has an International filing date of May 29, 2001, which designated the United States of America.

The invention relates to multifunctional (meth)acrylates with polycyclic or aromatic segments as well as materials prepared from them, in particular dental materials.

The aesthetic aspect in restorative dentistry is becoming increasingly important. In the anterior tooth area in particular, the patient can no longer be expected to receive a restoration which does not correspond to the natural tooth. The key to the aesthetic aspect is the opacity of the restoration material.

By restoration materials is meant within the meaning of this application in particular tooth filling materials, stump build-up materials, dental cements, dental varnishes as well as dental materials, such as veneering materials.

Dental restoration materials are based on curable monomers or monomer mixtures. Predominantly used in the state of the art are short-chained monomers based on (meth) acrylates, which lead to a not inconsiderable health risk through the release of non-polymerized residual monomers from the restoration material. There has therefore been no lack of attempts to switch to other monomer systems.

Thus for example the application DE-198 60 364 describes curable monomers based on cyclic siloxane (meth) acrylates. These are characterized by a high (meth)acrylate functionality which, in the case of curable materials prepared from same, leads to good physical properties.

Within the framework of the application DE-198 60 361, cyclic sol-gel-condensable siloxanes are described which, in curable materials prepared from same, lead to a low polymerization shrinkage and improved physical properties.

Overall, in the state of the art there is no lack of polymerizable materials which are characterized by low shrinkage and improved physical values; however, there is indeed a lack of curable materials which have improved aesthetic properties, in particular an opacity which guarantees the visual impression of natural tooth substance.

The object of the present application is to provide monomers with high molecular weight that allow the formulation of dental materials which in the cured state have a low opacity in order to guarantee the visual impression of natural tooth substance.

This object is achieved by the monomers according to the invention and the materials formulated from same, according to the claims.

An advantage of the monomers according to the invention, in addition to the fact that they have a high molecular weight, for example over 600 g/mol, preferably over 800 g/mol, is also a high (meth)acrylate functionality, for example over 2, preferably over 3 in the case of surprisingly low viscosity. They are therefore extremely well suited for the formulation of easily applicable materials.

The molecular weight of the monomers according to the invention can be so high until the limit of flowability is reached at 23° C.

The materials formulated from the monomers have a low polymerization shrinkage and very high mechanical strength. It is therefore also possible to formulate materials without using customary low-functional monomers based on pure (meth)acrylate, which for example reduces the risk to the patient caused by emerging residual monomers.

The materials formulated from the monomers have in particular an opacity of 80 to 90%, preferably 83 to 87%.

Furthermore, it is advantageous and surprising that the monomers are storage-stable despite their high number of acrylate or methacrylate groups per molecule.

The monomers according to the invention have the general formulae (1) or (2), the covalent bonding of a radical E to a siloxane backbone being common to the formulae:

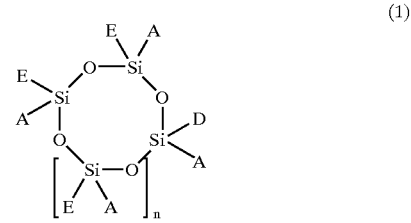

(1)

in which the following mean:

n=an integer from 0 to 10, preferably 1 to 5;

A=H or linear or branched $C_1$ to $C_{15}$ alk(en)yl, preferably methyl, ethyl, propyl, butyl, vinyl, ethinyl, allyl, or $C_3$ to $C_{15}$ cycloalk(en)yl, preferably cyclopentyl, cyclohexyl, cyclopentadienyl, cyclohexenyl, or $C_6$ to $C_{12}$ aryl, preferably phenyl, tolyl, xylyl, or $C_8$–$C_{18}$ alkaryl, preferably phenylethylenyl, of the named radicals, one or more C atoms in each case being able to be replaced by O, C=O, O(C=O), $SiR_2$ and/or NR, R being an aliphatic radical with 1 to 7 C atoms, in which one or more C atoms can be replaced by O, C=O and/or O(C=O);

D=E or a hydrocarbon structure which links 2 to 10, preferably 2 to 5 cyclosiloxane radicals, the structure being linear or branched or cyclic or polycyclic and containing 2 to 50, preferably 2 to 30 C atoms and additionally 0 to 30, preferably 0 to 20 other atoms from the group O, N, S, P, Cl, F, Br, I and to which 1 to 9, preferably 1 to 4 of the above-defined cyclosiloxane radicals according to formula (1), excluding D, are attached. Preferred radicals D are: di(prop-3-yl)ether, di(prop-3-yl)sulphide, di(prop-3-yl)amine, di(prop-3-yl) methylamine, tri(prop-3-yl)amine, di(prop-3-yl)urea, di(prop-3-yl)carbonate, ethylene glycol di(prop-3-yl) carbonate, diethylene glycol di(prop-3-yl)carbonate, ethylene glycol di(prop-3-yl)ether, diethylene glycol di(prop-3-yl)ether, 1,2-propanediol di(prop-3-yl)ether, 1,3-propanediol di(prop-3-yl)ether, 1,3-butanediol di(prop-3-yl)ether, 1,4-butanediol di(prop-3-yl)ether, 1,4-butenediol di(prop-3-yl)ether, 1,4-butinediol di(prop-3-yl)ether, 1,5-pentanediol di(prop-3-yl)ether, 1,6-hexanediol di(prop-3-yl)ether, 1,8-octanediol di(prop-3-yl)ether, 1,9-nonanediol di(prop-3-yl)ether, 1,10-decanediol di(prop-3-yl)ether, 1,12-dodecanediol di(prop-3-yl)ether, oxalic acid di(prop-3-yl)ester, malonic acid di(prop-3-yl)ester, succinic acid di(prop-3-yl)ester, adipinic acid di(prop-3-yl)ether, sebacic acid di(prop-3-yl)ether, 1,2-ethanediyl, 1,4-pentadienyl, 1,5-pentanediyl, 1,5-hexadienyl, 1,6-heptadienyl, 1,7-octadienyl, 1,8-nonadienyl, 1,9-decadienyl, 1,11-dodecadienyl, p-di(eth-2-yl)benzene, bis-(4-(prop-3-yl)oxyphenyl)-sulphone, bis-(4-(prop-3-yl)oxyphenyl)-ketone, bis-(4-(prop-3-yl) oxyphenyl)-methane, 1,1-bis-(4-(prop-3-yl)oxyphenyl)-ethane, 2,2-bis-(4-(prop-3-yl)oxyphenyl)-propane, 2,2-bis-(4-(prop-3-yl)oxyphenyl)-perfluoropropane, 2,2-bis-(4-(prop-3-yl)oxy-3,5-dibromophenyl)-propane, 3,3-bis-(4-(prop-3-yl)oxyphenyl)-pentane, 4,4-bis-(4-(prop-3-yl)

oxyphenyl)-heptane, 1,1-bis-(4-(prop-3-yl)oxyphenyl)-cyclopentane, 1,1-bis-(4-(prop-3-yl)oxyphenyl)-cyclohexane, 1,1-bis-(4-(prop-3-yl)oxyphenyl)-3,3,5-trimethyl-cyclohexane, 1,1,1-tris-(4-(prop-3-yl)oxyphenyl)-ethane, bis-((prop-3-yl-ether)oxy)-tricyclo [5.2.1.0$^{2,6}$]-decane;

E=A or a polymerizable group taken from the group G-C [(Q-T-L)$_a$(A)$_{3-a}$] and/or Q-L and optionally also X-T-L, up to 50%, preferably under 25% to 0% being permitted to correspond to the groups E in an average molecule A, with the proviso that in the case of molecules with only one siloxane ring, under 25% to 0% is permitted to correspond to the groups E in an average molecule A, and with the proviso that at least one group G-C[(Q-T-L)$_a$ (A)$_{3-a}$] and/or Q-L must be contained in the molecule;

G=linear, branched or cyclic $C_1$ to $C_{25}$, preferably $C_1$ to $C_{20}$ alk(en)ylene, arylene, alkarylene, arylalkylene, 0 to 5 C atoms being able to be replaced by a representative of the group O, S, N-A, C(O), C(O)O, OC(O), C(O)N, NC(O), OC(O)O, NC(O)O, OC(O)N, NC(O)N;

X=$C_1$ to $C_{10}$ alk(en)ylene, preferably ethylene, methylethylene, propylene, butylene, hexylene, ethenylene, propenylene;

Q=a radical containing an aromatic or polycyclic ring system in the chain, with 5 to 20, preferably 6 to 15 C atoms, which independently of each other also has 0 to 5 heteroatoms from the group O, N-A, S in the ring system;

T=O, N-A or a bi- or multivalent linear, branched or cyclic alcohol, amine or amino alcohol radical with 2 to 10 C atoms, preferably ethanediol diyl, 1,4,7-trioxaheptane-diyl, 1,4,7,10-tetraoxadecane-diyl, 1,4,7,10,13-pentaoxatridecane-diyl, glycerol-triyl, trimethylolpropane-triyl, pentaerythritol-tetryl;

L=an acrylate or methacrylate group;

a=2, 3.

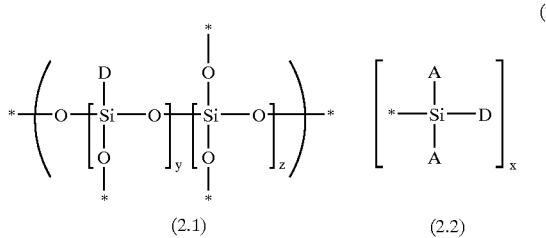

(2.1)        (2.2)

(2)

in which the following mean:

$x \leq 2+y+2z$;

y=0, 1, 2, 3, 4, 5, 6, 7, 8, preferably 0, 1, 2, 3;

z=0, 1, 2, 3, 4, 5, 6, 7, 8, preferably 0, 1, 2, 3;

A and D have the above meaning with the proviso that at least 3 of the radicals D in a molecule must have the meaning of G-C[(Q-T-L)$_a$(A)$_{3-a}$] or Q-L or X-T-L, and with the proviso that where y=z=0, at least 1 radical D has the meaning G-C[(Q-T-L)$_a$(A)$_{3-a}$];

and the "*" symbols in (2.1) signify the connection points for fragments (2.2) via their valency symbolized by a "*" to the fragment (2.1).

Each selection of a radical named several times in the context of this application via indices or via the multiple naming of the symbol is to be considered independently of every other selection from the same group. For example, the triple naming of a radical A in a molecule can mean that the position A can be replaced by methyl and ethyl and propyl in the same molecule.

Compounds according to formula (1) are based on cyclic siloxanes, one or more siloxane rings being able to occur per molecule.

Compounds according to formula (2) are based on linear or branched siloxanes, one or more siloxane radicals being able to occur per molecule.

The preparation of compounds of the general formulae (1) and (2) takes place preferably by hydrosilylation. Si—H-functional cyclosiloxanes and branched or linear siloxanes can thus be linked to C—C unsaturated organic structures (B. Marciniec: Comprehensive Handbook on Hydrosilylation, Pergamon Press, 1992). Desired monomer structures of the general formulae can be represented in this way.

Preferred Si—H-functional silicon core pieces for conversion to representatives of formulae (1) and (2) according to the invention are exemplary and include without limitation: $D^H_4$, $D^H_5$, $D^H_7$, $D^H_8$, a mixture of $D^H_x$, with x=4, 5, 6, 7, 8, 9, 10 (sum of these components >90%), $M^H_2$, $M^H_4Q$, $M^H_3T$, $M^H_3T^H$, $M^H_3T^{Ph}$, $M^H_8Q_8$, $T^H_8$ (silicon nomenclature according to Encyclopedia of Polymer Science and Engineering 2$^{nd}$ Ed. Vol. 15 p. 206ff; H=hydrido-functionalized, Ph=phenyl).

For example, 1,3,5,7-tetramethylcyclotetrasiloxane in a solvent such as toluene, under the influence of precious-metal catalysts such as (without limitation thereto) Speier catalysts, Karstedt catalysts but also Wilkinson catalysts, can be linked to four mol vinylbenzyl methacrylate to a representative of (1). Instead of the cyclotetrasiloxane, a commercially available mixture of SiH-cycles (Petrarch, M8830) (a mixture of $D^H_x$, with x=4, 5, 6) can also be used. Instead of vinylbenzyl methacrylate, other unsaturated compounds such as vinylnorbornenol methacrylate or allyl ethers, esters or amides of (meth)acrylate-functional Bisphenol-A derivatives, as well as endocyclic unsaturated and other (meth)acryl-functional organic molecules can be used. A further possibility according to the invention is to react the cyclosiloxane component not only with aromatic or polycyclic hydrosilylatable (meth)acrylates, but to do this in the mixture with aliphatic hydrosilylatable (meth)acrylates such as for example allyloxyethyl methacrylate or glycerol dimethacrylate allyl ether. However, products according to the invention are only the portions which carry at least one aromatic or polycyclic (meth)acrylate component in the molecule.

In the case of the reaction of polyfunctional SiH-cyclosiloxanes with likewise multiple C—C unsaturated organic structures (with the exception of the polymerizable double bonds), all C—C unsaturated functions of the organic structure can be saturated with in each case a cyclosiloxane ring through a suitable reaction procedure. However, pre-cross-linked intermediate products can also be produced by a different choice of stoichiometry or reaction procedure.

Both possibilities can be used independently of each other.

The structures shown in the following can be obtained in per se known manner by hydrosilylation of suitable Si—H compounds, for example with allyl or vinyl compounds. In the case of hydrosilylation, a mixture of isomeric adducts are obtained in various proportions (α- and β-adduct: see schema (I)) independently of the substrates and the catalyst. In each case, only one isomer is shown in the formulae, but all possibilities are meant.

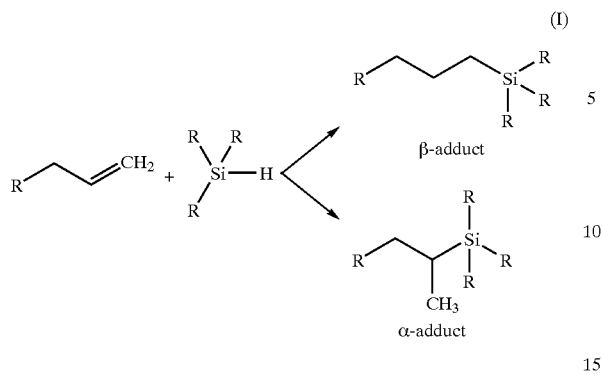

(I)

In addition to the methacrylates shown in the preferred examples, the corresponding acrylates as well as mixed types are also preferred.

Preferred representatives of formula (1) are:

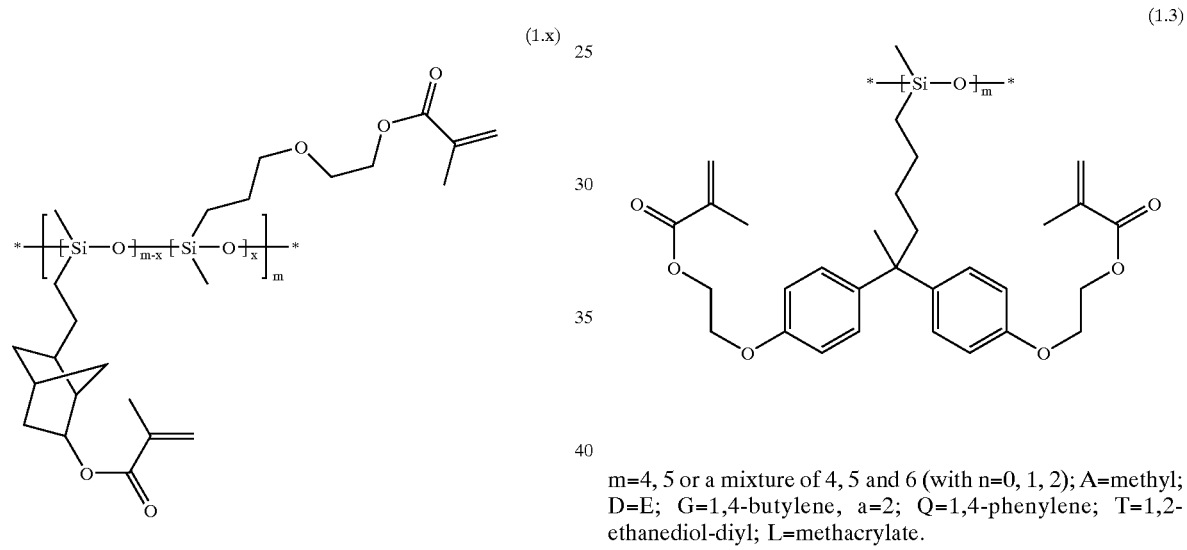

(1.x)

m=4, 5 or a mixture of 4, 5 and 6 (i.e.: n=0, 1, 2); x=1 to m−1, Q=2(3)-oxyl-bicyclo[2.2.1]hept-5-(1,2-ethanediyl)-yl; X=1,2-ethylene, T=1-oxa-1,3-propylene, L=methacrylate.

(1.1)

m=4, 5 or a mixture of 4, 5 and 6 (with n=0, 1, 2); Q=2(3)-oxyl-bicyclo[2.2.1]hept-5-(1,2-ethanediyl)-yl; L=methacrylate.

(1.2)

m=4, 5 or a mixture of 4, 5 and 6 (with n=0, 1, 2); Q=1,2-ethylene-(2-(4-methyleneoxyl-1,4(3)-phenylene); L=methacrylate.

(1.3)

m=4, 5 or a mixture of 4, 5 and 6 (with n=0, 1, 2); A=methyl; D=E; G=1,4-butylene, a=2; Q=1,4-phenylene; T=1,2-ethanediol-diyl; L=methacrylate.

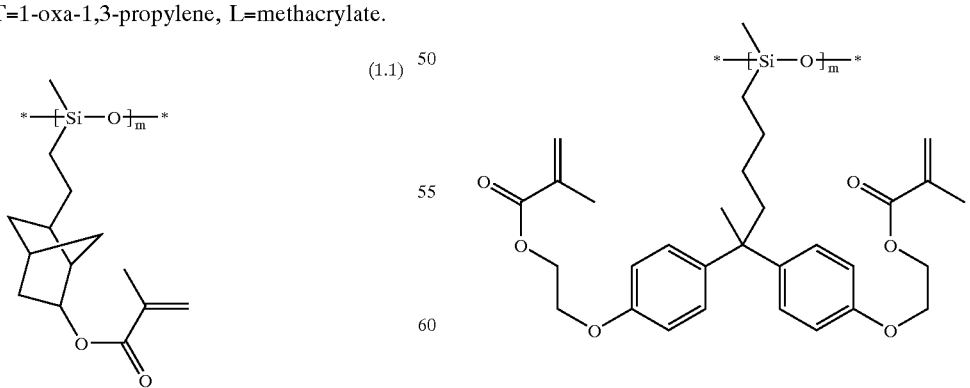

(1.4)

m=4, 5 or a mixture of 4, 5 and 6 (with n=0, 1, 2); A=methyl; D=E; G=1,2-ethylene, a=2; Q=1,4-phenylene; T=1,2-ethanediol-diyl; L=methacrylate.

(1.5)

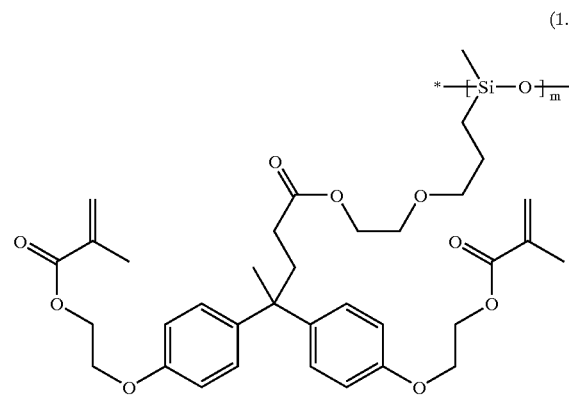

m=4, 5 or a mixture of 4, 5 and 6 (with n=0, 1, 2); A=methyl; D=E; G=4,7-dioxa-8-oxo-1,10-decylene, a=2; Q=1,4-phenylene; T=1,2-ethanediol-diyl; L=methacrylate.

(1.6)

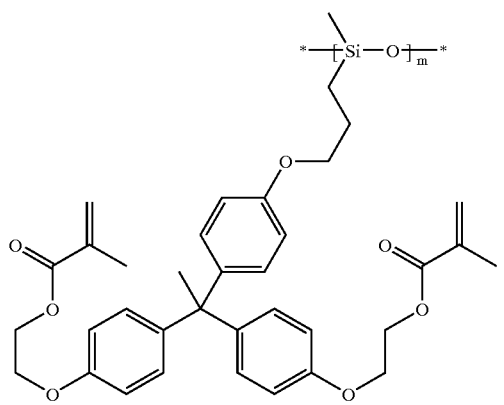

m=4, 5 or a mixture of 4, 5 and 6 (with n=0, 1, 2); A=methyl; D=E; G=4-oxa-1,4-butylene-4-(1,4-phenylene); a=2; Q=1,4-phenylene; T=1,2-ethanediol-diyl; L=methacrylate.

(1.8)

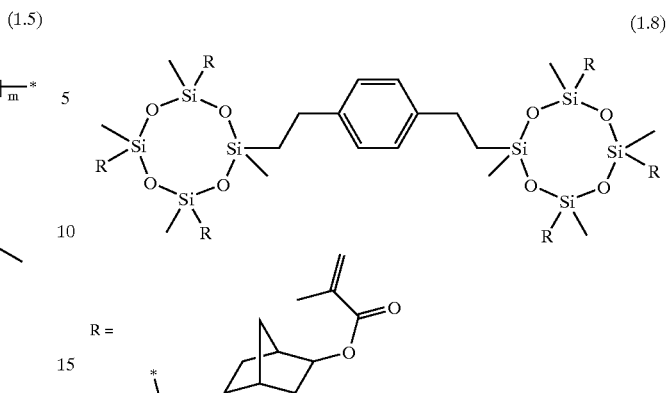

m=4 (with n=0); A=methyl; D=E, bis-[1,4-(1,2-ethanediyl)-phenylene); Q=2(3)-oxyl-bicyclo[2.2.1]hept-5-(1,2-ethanediyl)-yl; L=methacrylate.

(1.9)

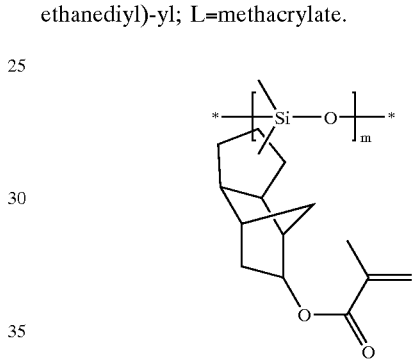

m=4, 5 or a mixture of 4, 5 and 6 (with n=0, 1, 2); A=methyl; D=E; Q=2(3)-oxyl-tricyclo[5.2.1.0$^{2,6}$]decane-6(7)-yl; L=methacrylate.

(1.7)

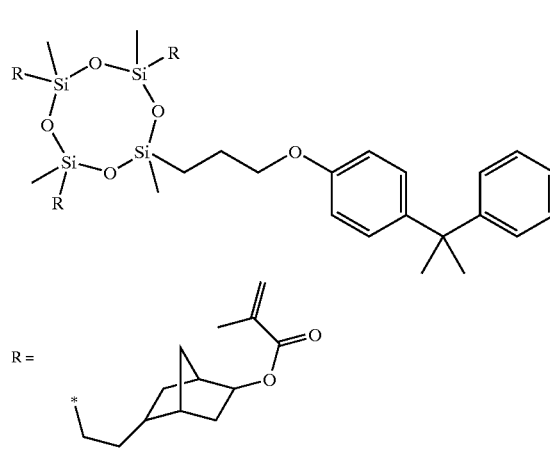

m=4 (with n=0); A=methyl; D=E, bis-[2,2-propanediyl-(4-(1,3-propylene-oxy)-1-phenylene); Q=2(3)-oxyl-bicyclo[2.2.1]hept-5-(1,2-ethanediyl)-yl; L=methacrylate.

Preferred representatives of formula (2) are:

(2.1)

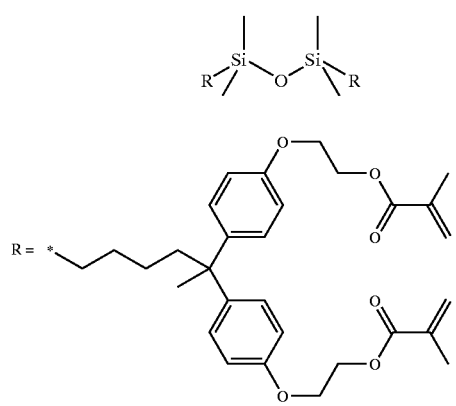

x=2; y=0; z=0; K=methyl, G-C[(Q-T-L)$_a$A$_{3-a}$]; G=1,4-butylene; A=methyl; a=2; Q=1,4-phenylene; T=1,2-ethanediol-diyl; L=methacrylate.

(2.2)

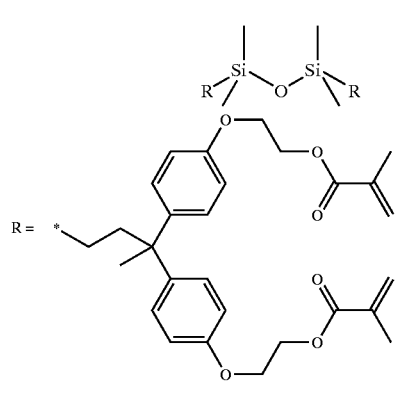

x=2; y=0; z=0; K=methyl, G-C[(Q-T-L)$_a$A$_{3a}$]; G=1,2-ethylene; A=methyl; a=2; Q=1,4-phenylene; T=1,2-ethanediol-diyl; L=methacrylate.

(2.3)

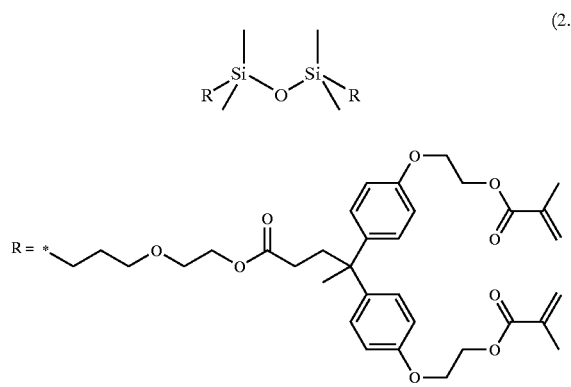

x=2; y=0; z=0; K=methyl, G-C[(Q-T-L)$_a$A$_{3-a}$]; $_{G=}$4,7-dioxa-8-oxo-1,10-decylene; A=methyl; a=2; Q=1,4-phenylene; T=1,2-ethanediol-diyl; L=methacrylate.

(2.4)

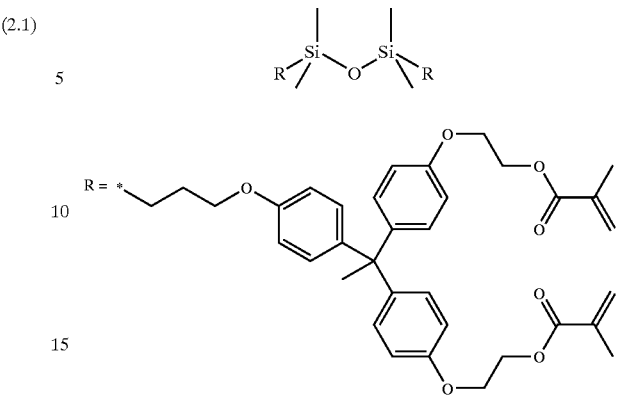

x=2; y=0; z=0; K=methyl, G-C[(Q-T-L)$_a$A$_{3-a}$]; $_{G=}$4-oxa-1,4-butylene-4-(1,4-phenylene; A=methyl; a=2; Q=1,4-phenylene; T=1,2-ethanediol-diyl; L=methacrylate.

(2.5)

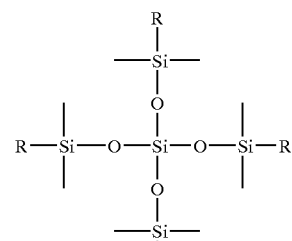

x=4; y=0; z=1; K=methyl, Q-L; Q=2(3)-oxyl-bicyclo[2.2.1]hept-5-(1,2-ethanediyl)-yl; L=methacrylate.

(2.6)

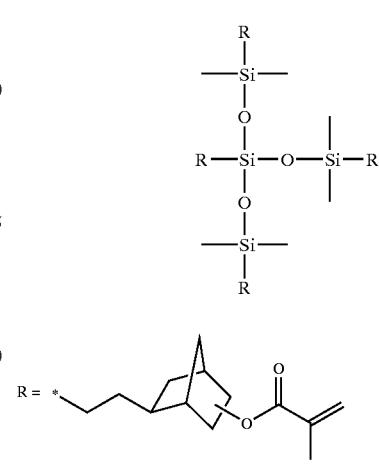

x=3; y=1; z=0; K=methyl, Q-L; Q=2(3)-oxyl-bicyclo[2.2.1]hept-5-(1,2-ethanediyl)-yl; L=methacrylate.

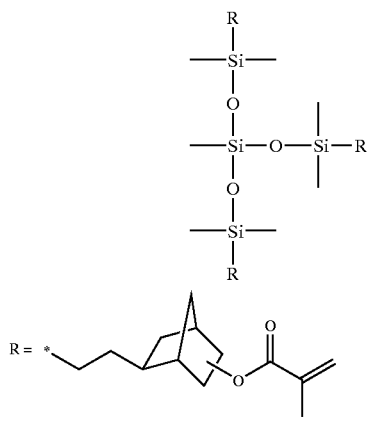

(2.7)

x=3; y=1; z=0; K=methyl, Q-L; Q=2(3)-oxyl-bicyclo[2.2.1]hept-5-(1,2-ethanediyl)-yl; L=methacrylate.

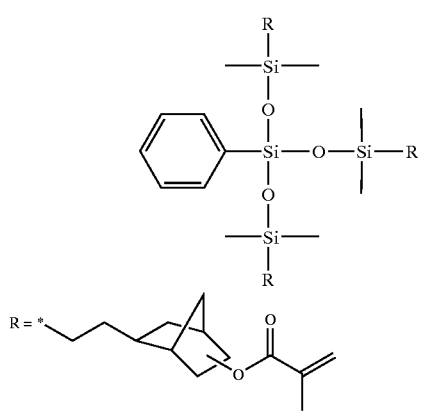

(2.8)

x=3; y=1; z=0; K=methyl, phenyl, Q-L; Q=2(3)-oxyl-bicyclo[2.2.1]hept-5-1,2-(ethanediyl)-yl; L=methacrylate.

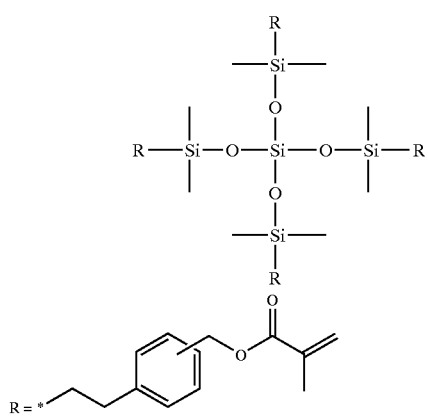

(2.9)

x=4; y=0; z=1; K=methyl, Q-L; Q=1,2-ethylene-(2-(4-methyleneoxyl-1,4(3)-phenylene); L=methacrylate.

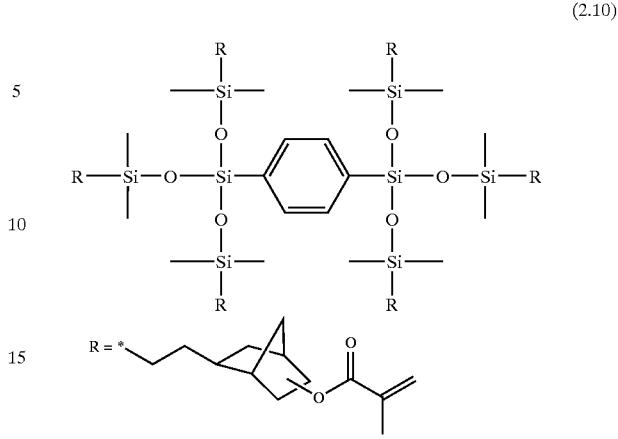

(2.10)

x=4; y=0; z=1; K=methyl, 1,4-phenylene, Q-L; Q=2(3)-oxyl-bicyclo[2.2.1]hept-5-(1,2-ethanediyl)-yl; L=methacrylate.

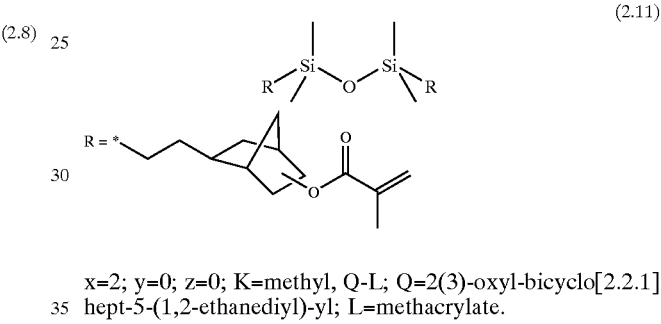

(2.11)

x=2; y=0; z=0; K=methyl, Q-L; Q=2(3)-oxyl-bicyclo[2.2.1]hept-5-(1,2-ethanediyl)-yl; L=methacrylate.

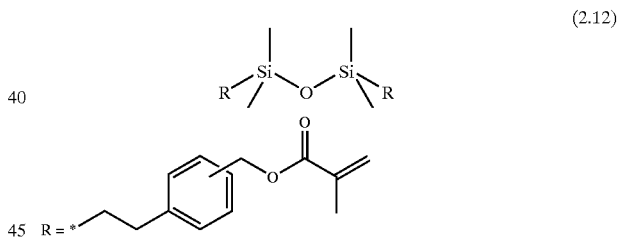

(2.12)

x=2; y=0; z=0; K=methyl, Q-L; Q=1,2-ethylene-(2-(4-methyleneoxyl-1,4(3)-phenylene); L=methacrylate.

According to the invention, there can also be prepared from the monomers according to formulae (1) and/or (2) curable materials containing:

(K1) 0 to 70, preferably 0 to 20 wt.-% monomers according to formula (1),
(K2) 0 to 70, preferably 0 to 20 wt.-% monomers according to formula (2),
(K3) 0 to 50, preferably 3 to 20 wt.-% co-monomers,
(K4) 20 to 90, preferably 70 to 85 wt.-% fillers,
(K5) 0.001 to 5, preferably 0.1 to 2 wt.-% initiators,
(K6) 0 to 20, preferably 0 to 5 wt.-% auxiliaries,
with the proviso that the sum of the components (K1) and (K2) is at least 10 wt.-%, preferably at least 12 wt.-%.

Co-monomers according to component (K3) are at least singly ethylenically unsaturated. Preferably used ethylenically unsaturated co-monomers are acrylates or methacrylates. Mono- and polyfunctional (meth)acrylate monomers are generally suitable. Typical representatives of this class of compounds (DE-A-43 28 960) are alkyl(meth)acrylates, including the cycloalkyl(meth)acrylates, aralkyl(meth) acrylates and 2-hydroxyalkyl (meth)acrylates, for example hydroxypropyl methacrylate, hydroxyethyl methacrylate, isobornyl acrylate, isobornyl methacrylate, butyl glycol methacrylate, acetyl glycol methacrylate, triethylene glycol dimethacrylate, polyethylene glycol dimethacrylate, 2-phenyl-ethyl methacrylate, 2-ethylhexyl methacrylate, cyclohexyl methacrylate, lauryl methacrylate and hexanediol di(meth)acrylate. Long-chained monomers based on Bisphenol A and glycidyl methacrylate, which are known from U.S. Pat. No. 3,066,112, or their derivatives resulting from addition of isocyanates can also be used. Compounds of the Bisphenyl-A-diethyloxy(meth)acrylate and Bisphenol-A-dipropyloxy(meth)acrylate type are also suitable. The oligoethoxylated and oligopropoxylated Bisphenol-A diacrylic and dimethacrylic acid esters can also be used. The diacrylic and dimethacrylic acid esters of bis(hydroxymethyl)-tricyclo[5.2.1.0$^{2,6}$]-decane named in DE-C-28 16 823 and the diacrylic and dimethacrylic acid esters of the compounds of bis(hydroxymethyl)-tricyclo [5.2.1.0$^{2,6}$]-decane extended with 1 to 3 ethylene oxide and/or propylene oxide units are also well suited.

Inorganic fillers can as a rule be used as fillers according to component (K4). Quartz, ground glasses, silica gels as well as pyrogenic silicic acids and precipitation silicic acids or their granules can be cited as examples. X-ray-opaque fillers are also preferably used, at least partially. These can for example be X-ray-opaque glasses, i.e. glasses which for example contain strontium, barium or lanthanum (e.g. according to U.S. Pat. No. 3,971,754) or some of the fillers consist of an X-ray-opaque additive, such as for example yttrium trifluoride, strontium hexafluorozirconate or fluorides of the rare earth metals (e.g. according to EP-A-0 238 025). For better incorporation into the polymer matrix, it is advantageous to hydrophobize the inorganic fillers. Customary hydrophobization agents are silanes, for example trimethoxymethacryloyloxypropyl silane or trimethoxyglycidyl silane.

The fillers preferably have an average grain size <20 $\mu$m, in particular <5 $\mu$m and an upper grain limit of 150 $\mu$m, preferably 70 $\mu$m and in particular 25 $\mu$m.

Mixtures of 5 to 25 wt.-% fillers with an average grain size of 0.02 to 0.06 $\mu$m and 65 to 85 wt.-% fillers with an average grain size of 1 to 5 $\mu$m are particularly preferably used.

Such systems which in a suitable period of time are able to form radicals are used as initiators according to component (K5). In the case of single-component materials, photoinitiators which can trigger the polymerization reaction through irradiation with UV or visible light are used for this.

Representatives of such photoinitiators are for example benzoin alkyl ethers, benzil ketals, acylphosphinic oxides or aliphatic and aromatic 1,2-diketone compounds, for example camphorquinone, the light polymerization being able to be accelerated by the addition of activators, such as tertiary amines or organic phosphites, in a manner known per se.

Suitable initiator systems for the triggering of the polymerization via a redox mechanism are for example the peroxide/amine or peroxide/barbituric acid derivatives systems or similar. When using such initiator systems, it is expedient to keep an initiator (e.g. peroxide) and a catalyst component (e.g. amine) ready separately. The two components are then homogeneously mixed with each other shortly before they are used.

Suitable auxiliaries according to component (K6) can for example normally be stabilizers, pigments or thinning agents used in the field of dentistry.

The preparation process of the materials disclosed here is preferably such that the liquid constituents are mixed with one another, the initiators, if they are not liquid, are introduced therein by stirring and the fillers are then added. A good homogenization can be achieved by kneading.

Two-component preparations which are cured by redox mechanisms are formulated such that the essential constituents of the redox initiation system are each introduced separately into a part of the two-component preparation. The distribution of the constituents of the overall preparation is based on the relevant storage properties and the desired mixing ratio.

The polymerizable materials are characterized by a high filling-substance content and associated high strength with simultaneously good processability.

The materials according to the invention are suitable in particular as materials for dental purposes, for example for the production of artificial teeth or temporary fittings, as coating products, for the gluing of substrates and as dental filling materials.

The materials according to the invention are usually introduced into receptacles such as tubular bags, single- or multi-chambered cartridges or capsules and other application units, for example blister packs or syringes, as known from the field of dentistry.

The invention is described in more detail in the following by examples without being limited thereby.

EXAMPLES

Preparation Example 1

Preparation of 1,3,5,7-tetrakis[2(3)-methacryloyl-bicyclo[2.2.1]heptane-5-(1,3-propanediyl]-1,3,5,7-tetramethyl-cyclotetrasiloxane (1.1)

10 g (41.6 mmol) 1,3,5,7-tetramethylcyclotetrasiloxane are dissolved in 50 ml of toluene and stirred with 34.3 g (166 mmol) 5-vinyl-2(3)-norbornanyl-methacrylate (prepared according to U.S. Pat. No. 3,927,116) and with Karstedt catalyst (3 to 3.5% Pt, 200 ppm Pt, ABCR) for 24 hours. The reaction is checked by means of IR and, if any Si—H bands are still present at approximately 2100 cm$^{-1}$, subsequently stirred until the bands disappear. After the customary working up and product isolation, 45.2 g (93%) of a bright-yellow viscous oil are obtained. Viscosity $\eta$ (23° C.)=70 Pa*s, $n_D^{20}$=1.496.

Preparation Example 2

Preparation of 1,3,5,7-tetrakis[4(3)-methacryloylmethylene-phenyl-1-(1,2-ethanediyl]-1, 3,5,7-tetramethyl-cyclotetrasiloxane (1.3)

10 g (41.6 mmol) of 1,3,5,7-tetramethylcyclotetrasiloxane are dissolved in 50 ml toluene and stirred with 33.7 g (166 mmol) 4(3)-vinylbenzyl-methacrylate (prepared according to Example 1 of EP-A-0 381 005) and with Karstedt catalyst (3 to 3.5% Pt, 200 ppm Pt, ABCR) for 24 hours. The reaction is checked by means of IR and, if any Si—H bands are still present at approximately 2100 cm$^{-1}$, subsequently stirred until the bands disappear. After the customary working up and product isolation, 45.2 g (93%) of a bright-yellow viscous oil are obtained. Viscosity $\eta$ (23° C.)=45 Pa*s, $n_D^{20}$=1.528.

Preparation Example 3

Preparation of 1,5-bis[2(3)-methacryloyl-bicyclo [2.2.1]heptane-5-(1,2-ethanediyl]-1,1,5,5-tetramethyl-3,3-bis-[2-(2(3)-methacryloyl-bicyclo [2.2.1]heptane-5-(1,2-ethanediyl)-2,2-dimethylsiloxy]-trisiloxane (2.5)

10 g (30.4 mmol) tetrakis-dimethylsiloxy-silane are dissolved in 50 ml toluene and stirred with 25.1 g (122 mmol)

5-vinyl-2(3)-norbornanyl-methacrylate (prepared according to Example XIV of U.S. Pat. No. 3,927,116) and with Karstedt catalyst (3 to 3.5% Pt, 200 ppm Pt, ABCR) for 24 hours. The reaction is checked by means of IR and, if any Si—H bands are still present at approximately 2100 cm$^{-1}$, subsequently stirred until the bands disappear. After the customary working up and product isolation, 45.2 g (93%) of a bright-yellow viscous oil are obtained. Viscosity η (23° C.)=12 Pa*s, $n_D^{20}$=1.492.

Preparation Example 4

Preparation of 1,4-bis[2-(1,3,5,7-tetramethyl-1,3,5,7-(2(3)-methacryloyl-bicyclo[2.2.1]heptane-5-(1,2-ethanediyl)-cyclotetrasiloxanyl)-1,2-ethanediyl]-benzene (1.8)

625 g (2.6 mol) 1,3,5,7-tetramethyl-cyclotetrasiloxane are introduced under reflux with 500 ml toluene and 0.8 g platinum on active carbon. 169 g divinylbenzene (1.3 mol; 80%, technical, Aldrich) are added to this. After the disappearance of the vinylic protons in the $^1$H-NMR, processing is carried out in the usual way. 587 g (92% of the theoretical value) of a colourless oil with the viscosity η (23° C.)=0.3 Pa*s and a refractive index of 1.471 are obtained.

21.7 g (0.105 mol) 5-vinyl-2(3)-norbornanyl-methacrylate and 50 ml toluene are reacted with Karstedt catalyst (3 to 3.5% Pt, 200 ppm Pt, ABCR). 11.3 g of the oil prepared in the previous paragraph are added dropwise at 50° C. and the mixture stirred for 24 hours. The reaction is checked by means of IR and, if any Si—H bands are still present at approximately 2100 cm$^{-1}$, stirred until the bands disappear. After the customary working up and product isolation, 29.0 g (88%) of a bright-yellow viscous oil are obtained. Viscosity η (23° C.)=78 Pa*s, $n_D^{20}$=1.480.

Preparation Example 5

Reaction of a Mixture of SiH-Cycles with a Mixture of Allyloxyethyl Methacrylate and 5-vinyl-2(3)-norbornanyl-methacrylate 10 g (166 mmol based on SiH) of a mixture of SiH-cycles (40% $D^H_4$, 45% $D^H_5$, the rest higher rings) are dissolved in 50 ml toluene and stirred with a mixture of 17.2 g (84 mmol) 5-vinyl-2(3)-norbornanyl-methacrylate (prepared according to U.S. Pat. No. 3,927,116), 14.3 g (84 mmol) allyloxyethyl methacrylate and hexachloroplatinic acid (dissolved in i-propanol) for 24 hours. The reaction is checked by means of IR and, if any Si—H bands are still present at approximately 2100 cm$^{-1}$, subsequently stirred until the bands disappear. After the customary working up and product isolation, 40 g (96%) of a bright-yellow viscous oil are obtained. Viscosity 2 Pa*s, $n_D^{20}$=1.486.

Application Examples, Comparison Example

The pasty preparations according to the application examples and the comparison example, the compositions of which are described in Table 1, were prepared in a 100-ml laboratory kneader.

The preparations were characterized in accordance with DIN ISO 4049 in respect of compression and bending strength.

The testpieces were prepared by irradiation of the materials introduced into moulds over a period of 40 seconds using the Elipar® II lighting device of ESPE Dental AG, Germany.

Following removal from the mould, the testpieces were stored in deionized water at 36° C. for a period of 24 hours, after which the mechanical properties were ascertained.

The volume shrinkage occurring during the radical polymerization was established by measuring the densities of the pasty preparations and of the cured compositions, using the Archimedes buoyancy method.

The opacity was measured by means of specimens with a defined height of 3.5 (+/−0.05) mm. These are prepared by filling the material to be checked into suitably high rings, evenly and free of bubbles, and illuminating it in the contact every 40 s by means of a lighting device (Elipar® II, ESPE) between plane, transparent matrices. The demoulded specimens are then subsequently hardened under vacuum in a lighting device (Visio® beta, ESPE) for another 15 mins. The opacity is then measured with the colour measuring device "HunterLab LabScan Spectralcolorimeter" of Hunter Lab Associates Laboratory, Inc., USA (Software SpecWare Software Version 1.10) and given by the device in %-values.

A summary of the property values ascertained for the cured preparations according to the application examples or the comparison example is shown in Table 2.

TABLE 1

Composition of the pasty preparations according to the application examples or the comparison example.

| Constituent | Application example No. | | | Comparison example No. | | |
|---|---|---|---|---|---|---|
| (Proportions in wt.-%) | A1 | A2 | A3 | V1 | V2 | V3 |
| (K1) Monomer according to preferred representative 1.1 | 22.5 | 10.3 | 11.3 | | | |
| (K1) Monomer according to preferred representative 1.8 | | 10.3 | | | | |
| (K1) Monomer according to preferred representative 2.5 | | | 11.3 | | | |
| 1,3,5,7-tetramethyl-1,3,5,7-tetrakis-(3-methacryloxypropyl)-cyclotetrasiloxane | | | | | 9.6 | 22.4 |
| 2,2-bis-4(3-hydroxypropoxyphenyl)propane-dimethacrylate | | | | 7.6 | | |
| 7,7,9-trimethyl-4, 13-dioxo-3, 14-dioxa-5, 12-diaza-hexadecane-1,16-dioldimethacrylate | | | | | 11.8 | |
| Bis-acryloylmethyltricyclo[5.2.1.0$^{2,6}$]decane | | | | 15.7 | | |
| (K2) Sr silicate glass, average particle size 1.2 micrometers, silanized | 73.9 | 76.4 | 74.0 | 35.0 | | 77.1 |
| (K2) Pyrogenic silicic acid | 3.1 | 2.5 | 2.9 | | | |
| (K2) Quartz powder, average particle size 1.5 micrometers, silanized | | | | 41.2 | 78.1 | |
| (K5) 2,2'-(3-methoxypropylnitrilo)diethanoldimethacrylate | 0.4 | 0.4 | 0.4 | 0.4 | 0.4 | 0.4 |
| (K5) 1,7,7-trimethyl-bicyclo[2.2.1]heptane-2,3-dion | 0.07 | 0.07 | 0.07 | 0.06 | 0.07 | 0.07 |

TABLE 2

Composition of the property values, ascertained for the cured preparations according to the application examples or the comparison example.

| Property | Application example No. | | | Comparison example No. | | |
|---|---|---|---|---|---|---|
| | A1 | A2 | A3 | V1 | V2 | V3 |
| Compression strength [MPa] | 380 | 373 | 405 | 411 | 416 | 345 |
| Bending strength [MPa] | 109 | 99 | 115 | 117 | 97 | 92 |
| Elasticity modulus [MPa] | 9678 | 8952 | 10025 | 8120 | 7348 | 4569 |
| Volume shrinkage [%] | 1.70 | 2.35 | 2.32 | 3.67 | 2.81 | 2.67 |
| Opacity in [%] | 84 | 80 | 80 | 82 | 96 | 98 |

The dental materials prepared using the monomers according to the invention show an opacity of approximately 85%, which makes possible the visual impression of natural tooth substance. The comparison examples are either clearly more opaque, as a result of which the restoration material has an unsatisfactory aesthetic appearance, or contain low-molecular monomers and therefore do not meet the toxicological requirements.

Outstanding physical values with optimal opacity can be achieved with the dental materials prepared from the high-molecular monomers according to the invention.

In particular the volume shrinkage is extremely low and the dental materials are therefore well suited for the permanent restorative care of a patient.

What is claimed is:

1. Monomers according to the following formula:

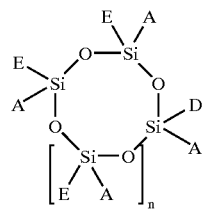

(1)

in which the following mean:

n=an integer from 0 to 10;

A=H or linear or branched $C_1$ to $C_{15}$ alk(en)yl, or $C_3$ to $C_{15}$ cycloalk(en)yl or $C_6$ to $C_{12}$ aryl or $C_8$–$C_{18}$ alkaryl, of the named radicals, one or more C atoms in each case being able to be replaced by O, C=O, O(C=O), and/or NR, R being an aliphatic radical with 1 to 7 C atoms, in which one or more C atoms can be replaced by O, C=O and/or O(C=O);

D=E or a hydrocarbon structure which links 2 to 10 cyclosiloxane radicals, the structure being linear or branched or cyclic or polycyclic and containing 2 to 50 C atoms and additionally 0 to 30 other atoms from the group O, N, S, F, Cl, F, Br, I and to which 1 to 9 of the above-defined cyclosiloxane radicals according to formula (1), excluding D, are attached;

E=A or a polymerizable group taken from the group G-C[(Q-T-L)$_a$(A)$_{3-a}$] and/or Q-L and optionally also X-T-L, up to 50% of groups E being permitted to correspond to A in an average molecule, with the proviso that in the case of molecules with only one siloxane ring, under 25% to 0% of the groups E are permitted to correspond to A in an average molecule, and with the proviso that at least one group G-C[(Q-T-L)$_a$(A)$_{3-a}$] and/or Q-L must be contained in the molecule;

G=linear, branched or cyclic $C_1$ to $C_{25}$ alk(en)ylene, arylene, alkarylene, arylalkylene, 0 to 5 C atoms being able to be replaced by a representative of the group O, S, N-A, C(O), C(O)O, OC(O), C(O)N, NC(O), OC(O)O, NC(O)O, OC(O)N, NC(O)N;

X=$C_1$ to $C_{10}$ alk(en)ylene;

Q=a radical containing an aromatic or polycyclic ring system in the chain, with 5 to 20 C atoms, which independently of each other also has 0 to 5 heteroatoms from the group O, N-A, S in the ring system, with the exception of tricyclo[5.2.1.0$^{2.6}$]decanyl-groups;

T=O, N-A or a bi- or multivalent linear, branched or cyclic alcohol, amine or amino alcohol radical with 2 to 10 C atoms;

L=an acrylate or methacrylate group;

a=2, 3.

2. Monomers according to the following formula:

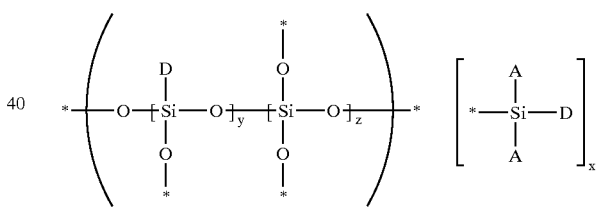

(2)

in which the following mean:

x≦2+y+2z;

y=0, 1, 2, 3, 4, 5, 6, 7, 8;

z=0, 1, 2, 3, 4, 5, 6, 7, 8;

A=hydrogen or linear or branched $C_1$ to $C_{15}$ alk(en)yl, or $C_3$ to $C_{15}$ cycloalk(en)yl or $C_6$ to $C_{12}$ aryl or $C_8$–$C_{18}$ alkaryl, of the named radicals, one or more C atoms in each case being able to be replaced by O, C=O, O(C=O), and/or NR, R being an aliphatic radical with 1 to 7 C atoms, in which one or more C atoms can be replaced by O, C=O and/or C(C=O);

D=E or a hydrocarbon structure which links 2 to 10 cyclosiloxane radicals, the structure being linear or branched or cyclic or polycyclic and containing 2 to 50 C atoms and additionally 0 to 30 other atoms from the group O, N, S, P, Cl, F, Br, I and to which 1 to 9 of the above-defined cyclosiloxane radicals according to formula (1), excluding D, are attached;

E=A or a polymerizable group taken from the group G-C[(Q-T-L)$_a$(A)$_{3-a}$] and/or Q-L and optionally also X-T-L, up to 50% of groups E being permitted to correspond to A in an average molecule, with the proviso that in the case of molecules with only one siloxane ring, under 25% to 0% of the groups E are permitted to correspond to A in an average molecule, and with the proviso that at least one group G-C[(Q-T-L)$_a$(A)$_{3-a}$] and/or Q-L must be contained in the molecule;

Q=a radical containing an aromatic or polycyclic ring system in the chain, with 5 to 20 C atoms, which independently of each other also has 0 to 5 heteroatoms from the group O, N-A, S in the ring system, with the exception of tricyclo[5.2.1.0$^{2.6}$]decanyl-groups; and L=an acrylate or methacrylate group with the proviso that at least three of the radicals D in a molecule must have the meaning of G-C[(Q-T-L)$_a$(A)$_{3-a}$] or Q-L or X-T-L, and with the proviso that where y=z=0, at least one radical D has the meaning of G-C[(Q-T-L)$_a$(A)$_{3-a}$].

3. Compositions containing (a) 0 to 70 monomers according to the following formula:

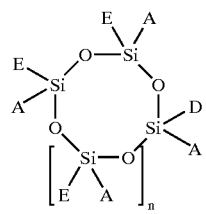

(1)

in which the following mean:

n=an integer from 0 to 10;

A=H or linear or branched C$_1$ to C$_{15}$ alk(en)yl, or C$_3$ to C$_{15}$ cycloalk(en)yl or C$_6$ to C$_{12}$ aryl or C$_8$–C$_{18}$ alkaryl, of the named radicals, one or more C atoms in each case being able to be replaced by O, C=O, O(C=O), and/or NR, R being an aliphatic radical with 1 to 7 C atoms, in which one or more C atoms can be replaced by O, C=O and/or O(C=O);

D=E or a hydrocarbon structure which links 2 to 10 cyclosiloxane radicals, the structure being linear or branched or cyclic or polycyclic and containing 2 to 50 C atoms and additionally 0 to 30 other atoms from the group O, N, S, P, Cl, F, Br, I and to which 1 to 9 of the above-defined cyclosiloxane radicals according to formula (1), excluding D, are attached;

E=A or a polymerizable group taken from the group G-C[(Q-T-L)$_a$(A)$_{3-a}$] and/or Q-L and optionally also X-T-L, up to 50% of groups E being permitted to correspond to A in an average molecule, with the proviso that in the case of molecules with only one siloxane ring, under 25% to 0% of the groups E are permitted to correspond to A in an average molecule, and with the proviso that at least one group G-C[(Q-T-L)$_a$(A)$_{3-a}$] and/or Q-L must be contained in the molecule;

G=linear, branched or cyclic C$_1$ to C$_{25}$ alk(en)ylene, arylene, alkarylene, arylalkylene, 0 to 5 C atoms being able to be replaced by a representative of the group O, S, N-A, C(O), C(O)O, OC(O), C(O)N, NC(O), OC(O)O, NC(O)O, OC(O)N, NC(O)N;

X=C$_1$ to C$_{10}$ alk(en)ylene;

Q=a radical containing an aromatic or polycyclic ring system in the chain, with 5 to 20 C atoms, which independently of each other also has 0 to 5 heteroatoms from the group O, N-A, S in the ring system, with the exception of tricyclo[5.2.1.0$^{2.6}$]decanyl-groups;

T=O, N-A or a bi- or multivalent linear, branched or cyclic alcohol, amine or amino alcohol radical with 2 to 10 C atoms;

L=an acrylate or methacrylate group;

a=2, 3, (b) 0 to 70 monomers according to the following formula:

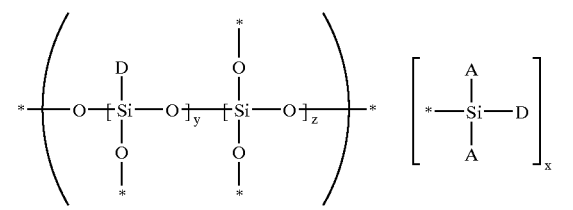

(2)

in which the following mean:

x≦2+y+2z;

y=0, 1, 2, 3, 4, 5, 6, 7, 8;

z=0, 1, 2, 3, 4, 5, 6, 7, 8;

A=hydrogen or linear or branched C$_1$ to C$_{15}$ alk(en)yl, or C$_3$ to C$_{15}$ cycloalk(en)yl or C$_6$ to C$_{12}$ aryl or C$_8$–C$_{18}$ alkaryl, of the named radicals, one or more C atoms in each case being able to be replaced by O, C=O, O(C=O), and/or NR, R being an aliphatic radical with 1 to 7 C atoms, in which one or more C atoms can be replaced by O, C=O and/or O(C=O);

D=E or a hydrocarbon structure which links 2 to 10 cyclosiloxane radicals, the structure being linear or branched or cyclic or polycyclic and containing 2 to 50 C atoms and additionally 0 to 30 other atoms from the group O, N, S, P, Cl, F, Br, I and to which 1 to 9 of the above-defined cyclosiloxane radicals according to formula (1), excluding D, are attached;

E=A or a polymerizable group taken from the group G-C[(Q-T-L)$_a$(A)$_{3-a}$] and/or Q-L and optionally also X-T-L, up to 50% of groups E being permitted to correspond to A in an average molecule, with the proviso that in the case of molecules with only one siloxane ring, under 25% to 0% of the groups E are permitted to correspond to A in an average molecule, and with the proviso that at least one group G-C[(Q-T-L)$_a$(A)$_{3-a}$] and/or Q-L must be contained in the molecule;

Q=a radical containing an aromatic or polycyclic ring system in the chain, with 5 to 20 C atoms, which independently of each other also has 0 to 5 heteroatoms from the group O, N-A, S in the ring system, with the exception of tricyclo[5.2.1.0$^{2.6}$]decanyl-groups; and L=an acrylate or methacrylate group with the proviso that at least three of the radicals D in a molecule must have the meaning of G-C[(Q-T-L)$_a$(A)$_{3-a}$] or Q-L or X-T-L, and with the proviso that where y=z=0, at least one radical D has the meaning of G-C[(Q-T-L)$_a$(A)$_{3-a}$], (c) 0 to 50 co-monomers, (d) 20 to 90 wt.-% fillers, (e) 0.001 to 5 wt.-% initiators, and (f) 0 to 20 auxiliaries, with the proviso that the sum of the components (a) and (b) is at least 10 wt.-%.

4. Compositions according to claim 3 with an opacity of 80 to 90%.

5. A method for the preparation of a dental material comprising curing monomers according to claim 1 to produce a dental material having an opacity which provides a visual impression of a natural tooth substance.

6. A receptacle containing at least one material including monomers according to any one of claims 1 and 2.

7. A receptacle containing at least one composition according to any one of claims 3 and 4.

8. A method for the preparation of a curable material comprising curing cyclic siloxanes containing at least one side chain G-C[(Q-T-L)$_a$(A)$_{3-a}$] and/or Q-L according to claim 1 or linear siloxanes containing at least one side chain G-C[(Q-T-L)$_a$(A)$_{3-a}$] and/or Q-L according to claim 2 to produce a curable material having an opacity of 80 to 90%.

9. A method for the preparation of a dental material comprising curing monomers according to claim 2 to produce a dental material having an opacity which provides a visual impression of a natural tooth substance.

10. A method for the preparation of a dental material comprising curing compositions according to claim 3 to produce a dental material having an opacity which provides a visual impression of a natural tooth substance.

11. A method for the preparation of a dental material comprising curing compositions according to claim 4 to produce a dental material having an opacity which provides a visual impression of a natural tooth substance.

12. Monomers according to claim 1 or 2 wherein:

D=E or a hydrocarbon structure which links 2 to 5 cyclosiloxane radicals, the structure being linear or branched or cyclic or polycyclic and containing 2 to 50 C atoms and additionally 0 to 30 other atoms from the group O, N, S, P, Cl, F, Br, I and to which 1 to 9 of the above-defined cyclosiloxane radicals according to formula (1), excluding D, are attached.

13. Monomers according to claim 1 wherein:

E=A or a polymerizable group taken from the group G-C[(Q-T-L)$_a$(A)$_{3-a}$] and/or Q-L and optionally also X-T-L, 25% to 0% of groups E being permitted to correspond to A in an average molecule, with the proviso that in the case of molecules with only one siloxane ring, under 25% to 0% of the groups E are permitted to correspond to A in an average molecule, and with the proviso that at least one group G-C[(Q-T-L)$_a$(A)$_{3-a}$] and/or Q-L must be contained in the molecule.

* * * * *

UNITED STATES PATENT AND TRADEMARK OFFICE
CERTIFICATE OF CORRECTION

PATENT NO.       : 6,852,795 B2                                    Page 1 of 1
APPLICATION NO.  : 10/296491
DATED            : February 8, 2005
INVENTOR(S)      : Peter Bissinger It is certified that error appears in the above-identified patent and that said Letters Patent is hereby corrected as shown below:

<u>On Title Page, Col. 2, on (Foreign Patent Documents)</u>
Line 8, delete "JP" and insert -- EP --, therefor.
Line 9, delete "JP" and insert -- EP --, therefor.
Line 10, delete "JP" and insert -- EP --, therefor.

<u>Column 2</u>
Line 8, after "formulae" delete ":" and insert -- . --, therefor.

<u>Column 9</u>
Line 65, delete "$_G$=4,7" and insert -- G=4,7 --, therefor.

<u>Column 10</u>
Line 20, delete "$_G$=4-oxa" and insert -- G=4-oxa --, therefor.

<u>Column 17</u>
Line 55, in Claim 1, after "S," delete "F," and insert -- P, --, therefor.

Signed and Sealed this

Sixth Day of May, 2008

JON W. DUDAS
*Director of the United States Patent and Trademark Office*